US006686208B2

(12) United States Patent
Meusel et al.

(10) Patent No.: US 6,686,208 B2
(45) Date of Patent: *Feb. 3, 2004

(54) DEVICE AND METHOD FOR CARRYING OUT FLUORESENCE IMMUNOTESTS

(75) Inventors: Markus Meusel, Münster (DE); Dieter Trau, Münster (DE); Andreas Katerkamp, Münster (DE)

(73) Assignee: Institut fur Chemo- und Biosensorik Munster e.V., Munster (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/212,954

(22) Filed: Aug. 6, 2002

(65) Prior Publication Data
US 2003/0032199 A1 Feb. 13, 2003

Related U.S. Application Data

(63) Continuation-in-part of application No. 09/381,213, filed as application No. PCT/DE98/00729 on Mar. 11, 1998, now abandoned.

(30) Foreign Application Priority Data

Mar. 18, 1997 (DE) .......................... 197 11 281

(51) Int. Cl.[7] ...................... G01N 33/53; G01N 33/543; C12M 1/00
(52) U.S. Cl. .................. 436/518; 436/164; 436/170; 436/172; 436/528; 436/529; 436/530; 436/805; 436/807; 435/4; 435/7.1; 435/7.9; 435/7.92; 435/174; 435/177; 435/178; 435/179; 435/180; 435/287.1; 435/287.2; 435/287.9; 435/288.5; 435/808; 435/968; 435/969; 422/52; 422/57; 422/58; 422/60; 422/68.1; 422/82.08; 422/82.09; 422/82.11; 333/210
(58) Field of Search .................. 333/210; 356/73.1, 356/129, 130, 246, 318, 337, 339, 340, 369, 445, 477, 481, 484, 517, 519, 521, 927, 928; 422/52, 57, 58, 60, 68.1, 82.08, 82.09, 82.11; 435/4, 7.1, 7.9, 7.92, 174, 177, 178, 179, 180, 287.1, 287.2, 287.9, 288.5, 808, 968, 969; 436/164, 170, 172, 518, 528, 529, 530, 805, 807

(56) References Cited

U.S. PATENT DOCUMENTS 3,939,350 A * 2/1976 Kronick et al. ............. 250/365
4,810,658 A * 3/1989 Shanks et al. ............... 436/172
4,978,503 A * 12/1990 Shanks et al. ............... 422/58
5,071,746 A * 12/1991 Wilk et al. ................. 435/7.94

(List continued on next page.)

FOREIGN PATENT DOCUMENTS

DE        38 14 370 A      11/1989
DE        41 21 493         1/1993
DE        196 11 025        9/1997

(List continued on next page.)

OTHER PUBLICATIONS

Badley et al.; "Optical Biosensors for Immunoassays: The Fluorescence Capillary–Fill Device," *Phil. Trans. R. Soc. Lond.*, B316, pp 143–160 (1987).

Christensen et al. "Analysis of Excitation and Collection Geometries for Planar Waveguide Immunosensors," *Proc. SPIE–Int. Soc. Opt. Eng.*, 1886, pp 2–8 (1993).

*Primary Examiner*—Long V. Le
*Assistant Examiner*—Kartic Padmanabhan
(74) *Attorney, Agent, or Firm*—Leydig Voit & Mayer, Ltd.

(57) ABSTRACT

The invention relates to devices and methods for carrying out quantitative fluorescence immunoassays using evanescent field excitation. Light from at least one light source is directed onto the boundary between two media which have differing refractive indices. The light source emits practically monochromatic light with a wavelength suitable for exciting a marking substance. The light is directed onto a boundary surface disposed between an optically transparent base plate, the refractive index of which is greater than that of the material above the boundary surface, and a receiving region for the sample. The receiving region is covered with a covering plate on the side disposed opposite the base plate, there being arranged between the base plate and covering plate at least one functional layer. A detector for detecting the fluorescent light is disposed on the same side of the base plate as the light source.

17 Claims, 17 Drawing Sheets

U.S. PATENT DOCUMENTS

| | | | | |
|---|---|---|---|---|
| 5,164,589 A | * | 11/1992 | Sjodin | 250/227.24 |
| 5,313,264 A | * | 5/1994 | Ivarsson et al. | 356/73 |
| 5,344,784 A | * | 9/1994 | Attridge | 436/518 |
| 5,512,492 A | * | 4/1996 | Herron et al. | 436/518 |
| 5,573,956 A | * | 11/1996 | Hanning | 436/518 |
| 6,274,872 B1 | * | 8/2001 | Katerkamp | 250/458.1 |
| 6,440,748 B1 | * | 8/2002 | Katerkamp et al. | 436/518 |

FOREIGN PATENT DOCUMENTS

| | | | |
|---|---|---|---|
| EP | 0 341 927 A1 | * | 11/1989 |
| EP | 0 361 127 A1 | * | 12/1994 |
| WO | WO 90/05295 A | | 5/1990 |
| WO | WO 90/06503 A | | 6/1990 |
| WO | WO 90/11525 A1 | * | 10/1990 |
| WO | WO 94/27137 A | | 11/1994 |
| WO | WO 98/02732 A1 | * | 12/1998 |

* cited by examiner solid phase with immobilised analyte displacement and detection on the detector layer

DEVICE AND METHOD FOR CARRYING OUT FLUORESENCE IMMUNOTESTS

This is a continuation-in-part of U.S. patent application Ser. No. 09/381,213 (here by incorporated in its entirety by reference), filed on Nov. 18, 1999, now abandoned, which is a national stage application of PCT/DE98/00729, filed on Mar. 11, 1998, and claims the benefit of German Patent DE 197 11 281.1, filed on Mar. 18, 1997 (hereby incorporated in its entirety by reference).

TECHNICAL FIELD

The present invention relates generally to methods for quantifying amounts of chemical or biochemical substances, and, more particularly, to quantitative fluorescence assays that use evanescent field excitation.

BACKGROUND OF THE INVENTION

Fluorescence immunoassays or even florescence immunosensors have already been generally used for a long time, and they serve, mainly in a liquid sample matrix, to quantify an unknown amount of a specific chemical or biochemical substance. Antibodies are here selectively bound to the substance to be determined. The substance to be determined is also referred to by the expert as an antigen. In the fluorescence immunoassays, the analyte-specific antibodies are marked with a marking substance which is optically excited at a certain substance-specific wavelength $\lambda_{ex}$ and the fluorescent light with a different wave length, which is generally greater, is used with a suitable detector with evaluation of the intensity of the fluorescent light. The exploitation of the evanescent field excitation in carrying out such fluorescence immunoassays, or respectively in the fluorescence immunosensors, is already part of prior art. Thus different solutions have already been described in WO 94/27137, by R. A. Badlay, R. A. L. Drake, I. A. Shanks, F. R. S., A. M. Smith, and P. R. Stephenson in "Optical Biosensors for Immunoassays; Fluorescence Capillary-Fill Device", Phil. Trans. R. Soc. Lund. B 316, 143 to 160 (1987) and D. Christensen, S. Dyer, D. Fowers, and J. Herron, "Analysis of Exitation and Collection Geometries for Planar Waveguide Immunosensors", Proc. SPIE-Int. Soc. Opt. Eng. Vol. 1986, Fiber Optic Sensors in Medical Diagnostics, 2 to 8 (1993).

In addition, in WO 90/05295 A1, an optical biosensor system is described. In this system, one or more samples are guided, with the use of pumps and valves, through ducts to one or more flow-through measuring cells. These flow-through measuring cells are open upwards and biomolecules can be quantitatively detected by an optical structure disposed above them. For measuring successive new samples, considerable purification outlay is consequently required, in order to avoid measuring errors. A possibly necessary preparation of such a sample generally has to be carried out externally of this system, before the actual measuring, since no elements or measures suitable for this purpose are named.

In WO 90/06503, a sensor is described in which the excitation light is directed at an appropriate angle through an optically transparent substrate onto a boundary surface to an optically transparent buffer layer. Above which an additional waveguide layer is applied, to which in turn the analytes to be determined can be bound.

The refractive index of the buffer layer is here smaller than that of the substrate and of the waveguide. At the boundary layer substrate/buffer, total reflection comes about through appropriate choice of the angle of the excitation light, and, via the evanescent field produced here, the excitation light is coupled into the waveguide situated above the buffer layer. The light coupled into the waveguide is guided via total reflection in the waveguide, and the evanescent field forming during this process is correspondingly used for fluorescence excitation.

The sample can be received in one or more cavities, the corresponding dimensions of such a cavity being only restricted to the extent that its size renders possible the transport of the samples in the cavities by means of capillary force. After the sample has been received in the cavities, no further flow or movement of the sample takes place.

The known solutions have, however, in general the disadvantage that they are only suitable for specific assay formats and an expensive structure with corresponding process management is necessary.

It is therefore an object of the invention to create a way to carry out, with a very simply constructed device, quantitative fluorescence immunoassays with different biochemical assays.

SUMMARY OF THE INVENTION

This object preferably is achieved according to the invention. Advantageous embodiments and developments of the invention will be apparent from the description of the invention provided herein.

In a device described in the not prior-published DE 196 11 025, light of at least one light source is directed at an angle $\alpha$ on the boundary surface of two media with differing refractive indices. Here a light source is selected which emits practically monochromatic light with a wavelength which is suitable for exciting the marking substance, in this case the fluorophore. Particularly suitable as the light source here are laser diodes, since they have a suitable beam profile and sufficient luminous efficiency, with a small constructional size and low energy consumption.

However, other light sources which emit monochromatic light can also be used.

The angle $\alpha$, at which the emitted light is sent to the boundary surface, determines, besides the refractive index of the material disposed in the beam path before the boundary surface, and the material adjoining same, together with the wavelength of the light, the penetration depth d for the evanescent field. The refractive index $n_1$ of the material which is disposed in the beam path before the boundary surface must render possible total reflection at the boundary surface and should therefore be greater than the refractive index $n_2$ of the other material disposed thereafter. The angle $\alpha$ is preferably so chosen that the following is true: $\sin(\alpha) > n_2/n_1$. If this precondition is met, all the light is reflected at the boundary surface and thus total reflection is achieved. However, when this condition is met, a relatively small portion of the light penetrates through the boundary surface into the material, which is disposed in the beam path after the boundary surface, and the evanescent field is produced. Through the evanescent field, only those marking substances are optically excited which are located in the immediate proximity of the boundary surface. For carrying out fluorescence immunoassays, the result of this is that only the marking substances of the antibodies or antigens which are bound to the surface of the boundary surface are excited. The fluorescence intensity of the light emitted by these fluorophores is thus directly proportional to the concentration of the marked antibodies or antigens bound to the surface, and, according to the biochemical assay used, proportional or inversely proportional to the antigen concentration.

Now the device described in DE 196 11 025 uses at least one light source, which emits practically monochromatic light and directs this at an angle providing the penetration depth d for the evanescent field, onto a base plate which is transparent for this light. The refractive index $n_1$ of the base plate should be greater than 1.33. On the other side of the base plate, a cuvette-shaped receiving region is formed between a covering plate. Between the base plate and the cuvette-shaped receiving region is formed said boundary surface and the evanescent field can act with the given penetration depth d within the cuvette-shaped receiving region on marked chemical or biochemical partners, bound to the surface, of a general receptor-ligand system and excite the fluorophores used as the marking substance.

The fluorescence so caused is measured at the corresponding intensity with a detector. The detector is here disposed on the same side of the base plate as the light source.

As the detector, a single light-sensitive detector, a linear or a surface arrangement of a plurality of light-sensitive detectors can here be used.

It is also described there that it is advantageous to direct polarised light onto the sample to be determined. For this purpose, a polarizer can be arranged in the beam path of the light, following the light source.

The spacer and possibly the separating layers to be used are 0.001 to 10 mm thick, preferably 50 µm, and a recess in the spacer forms the receiving region for the sample. Spacer and separating layers can preferably be a biocompatible adhesive film, which is designed to adhere on both sides.

The method according to the invention is based essentially on the fact that a defined sample volume is guided through the cuvette-shaped receiving region and there subjected to an evanescent field excitation, as has been described already. The sample volume can here be guided through the cuvette-shaped receiving region and the functional layer(s) by means of suction, pressure, and capillary forces.

In an advantageous embodiment, there is provided in a covering plate at least one inlet aperture, into which a sample container can be inserted or disposed, the aperture being so disposed in the covering plate that a connection may be produced between inlet aperture or sample container and receiving region. In addition, there is a second aperture which is also connected with the cuvette-shaped receiving region and represents an outflow.

The second aperture can also be provided in the covering plate. An external pump can be connected to this second aperture, or an internal pump can be inserted.

The invention is characterised by the fact that a relatively simply constructed basic pattern of a device according to the invention can be altered or used in the most varied form. Thus the essential elements, base plate, covering plate and spacer with cuvette-shaped receiving region, can be combined in the most varied way through functional layers, the separating layers, disposed if necessary in between yet allowing the sample to flow through. One or more of such functional layers can, however, also be arranged in the inflow region for the sample into the receiving region, an inlet aperture or a connection between a sample container which may be inserted into the inlet aperture, or the connection of inlet aperture and receiving region, forming part of this inflow region.

With the invention, the different assay formats may be carried out and thereby high- and low-molecular compounds can be equally detected. All known assay formats, such as sandwich-titration/competition and displacement formats, can be carried out.

For the case that separating layers are used between functional layers, or enclosing same, these separating layers must have corresponding openings, such that it is guaranteed that the sample volume can flow through the entire device. As separating layers, adhesive films can be used, for example, into which openings are produced by stamping.

The invention will be described in more detail below, by way of example.

DETAILED DESCRIPTION OF THE INVENTION

Figure 1:
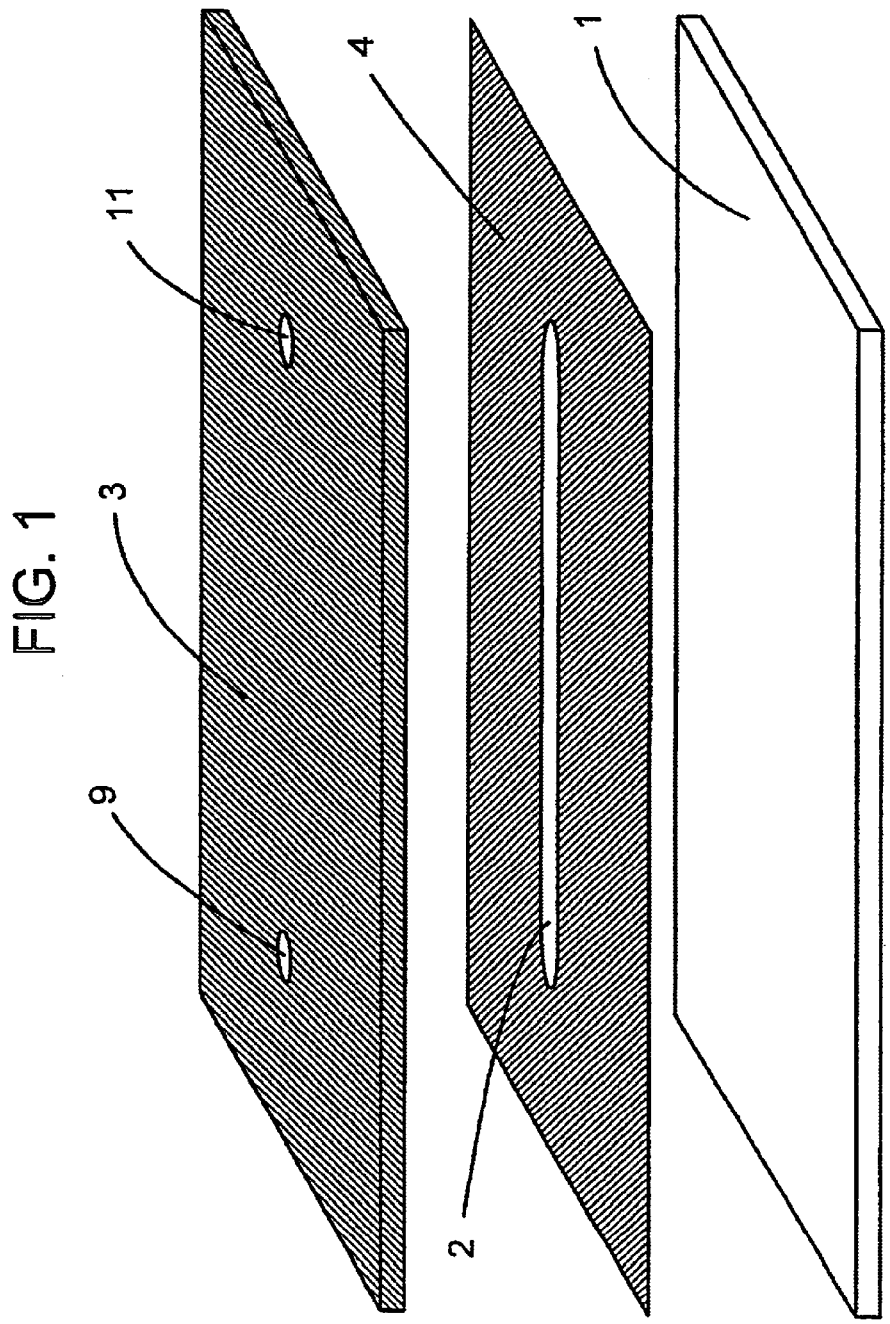
FIG. 1 a portion of the device according to the invention for receiving a sample.

In FIG. 1 is represented the basic structure of a portion of the device according to the invention. The three parts shown there, the base plate 1, the spacer 4 and the covering plate 3, can be connected to one another before the fluorescence immunoassay is carried out, or form already a completely finished unit and resemble in their structure a flow-through cell and a measuring cuvette.

The base plate 1 here consists of a highly refractive transparent material, such as, for example, glass or a plastics material, such as a polymer (PMMA or PC) with a refractive index $n_1>1.33$. The thickness of the base plate can be within a range of 0.01 to 10 mm, preferably between 0.5 and 1 mm.

The spacer 4 is preferably a thin foil, which is provided on both sides with an adhesive film, or a thin adhesive film may be applied firstly to the base plate 1 and secondly to the covering plate 3. The total thickness of the spacer including the adhesive used should be in a range between 0.001 and 10 mm, preferably between 0.01 and 0.2 mm, and a thickness of 50 µm is most particularly preferred. An opening is worked into the spacer 4 and forms a cuvette-shaped receiving region 2.

In FIG. 1, the covering plate 3 can also be recognised in which continuous apertures 9 and 11 have been formed, as bores in this example. The function of these will be returned to later. Apertures 9 and 11 are here so disposed that they at least partially overlap the area of the receiving region 2 of the spacer 4. The spacer 4 can preferably also consist of a biocompatible adhesive film, which is preferably provided on both sides with a detachable protective layer and is already commercially available.

Figure 2:
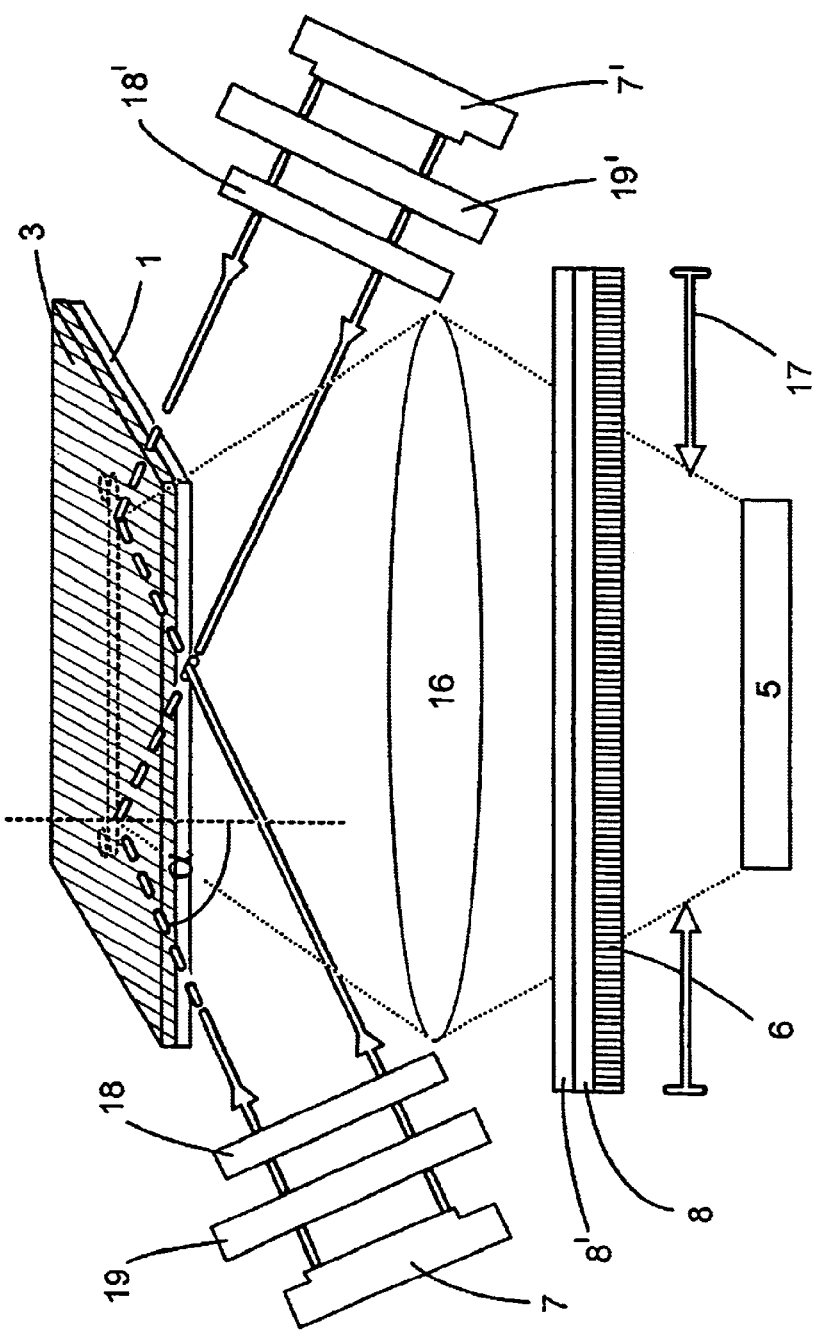
FIG. 2 a schematic representation of an embodiment of a device configured according to the invention, with two light sources.

An exemplary system is shown in FIG. 2. An analyte sample is guided through a receiving region on the base plate 1. Source 7 emits practically monochromatic light onto the receiving region of the base plate 1. That light causes a marking substance in the sample on the receiving region to emit fluorescence. The fluorescence is emitted in all directions. Unlike in previous systems, no waveguide is used to direct the emitted fluorescence to the detector 5. Instead, a portion of the emitted fluorescence travels through the base plate 1 and then through the air, downward in FIG. 2, where it is focused by a lens 16 onto the fluorescence detector 5. In some embodiments, a polarisator 6 and aperture 17 aid in directing the fluorescence to the detector 5.

The example represented in FIG. 2 of a device configured according to the invention uses two light sources 7, 7', filters 19, 19' and polarizers 18, 18'. The light source 7' emits light of a wavelength which is different from that of the first light source 7. In this example, polarised light is preferably used. The device shown in FIG. 2 can be advantageously used when differing marking substances, which can be excited at different wavelengths, are used. Examples of these are the fluorophores Cy5 and Cy7. To excite the fluorophore Cy5, a laser diode is used with light of a wavelength between 635 and 655 nm, and for the fluorophore Cy7, a laser diode which emits light with a wavelength between 730 and 780 nm.

The measuring takes place with this embodiment by way of the diodes 7, 7' being either switched alternating, or, for example, correspondingly synchronised choppers being used, such that it is ensured that respectively only light from one light source 7 or 7' can reach the sample to excite it and thus no falsifications occur.

However, since here two different fluorescence signals have to pass the same filter, a wideband filter 8 can no longer be used. Therefore, two filters 8, 8' should be disposed in succession, which selectively block the wavelengths of the exciting light sources 7, 7'. Notch filters can, for example, be used for this purpose.

With this arrangement, a reference signal can first be obtained which renders possible an internal calibration of the measuring signal. For reference measurement, a reference antibody is used which is not directed against an antigen from the sample. The reference antibody is first quantified and made distinguishable, with a different marking substance, from the analyte-specific antibody Ak to be determined. The amount of reference antibody actually bound to the surface can be determined with a second light source 7', which causes light of a fluorescence of the different marking substance, a second scattered light filter 8' and the detector 5. With this determination, the losses of the marked analyte-specific antibodies Ak or antigens Ag, not bound to the surface, can be taken into account.

Besides obtaining a reference signal, however, two immunoassays, running independently of one another, can be carried out, the difference coming about with the aid of the different fluorophores.

Figure 3:
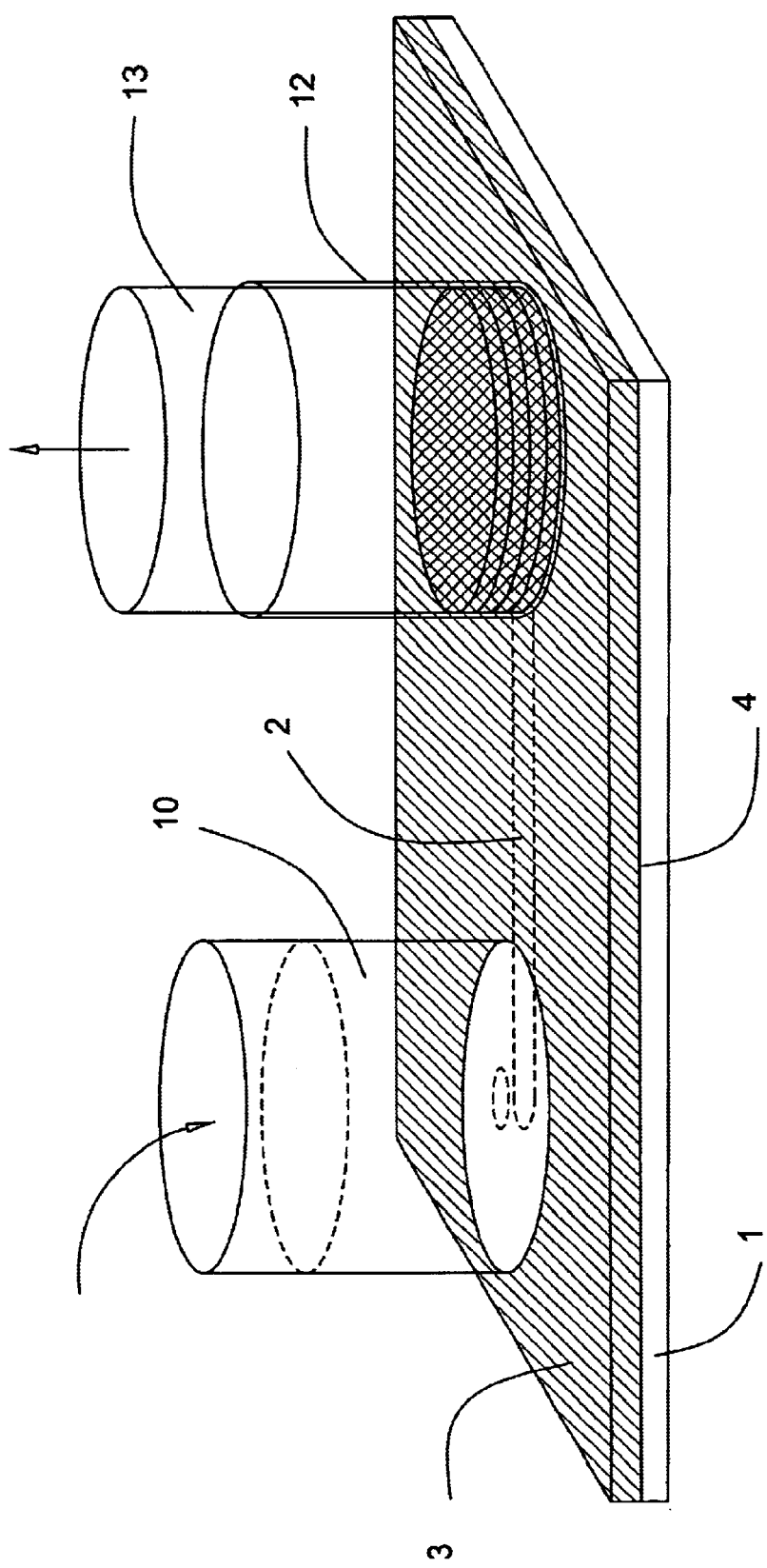
FIG. 3 a device with sample container.

In FIG. 3 is shown how a sample container 10 is disposed towards aperture 9 in the covering plate 3 and thus a connection may be made between sample container 10 and the receiving region 2 via aperture 9. Here the sample container 10 forms the container in which the known amount of biocomponent marked with the marking substance fluorophore is mixed in the sample to be determined. Here the sample container 10 can clearly define the sample volume and thus, with a fixed and known sample volume, a quantitative statement about the antigen concentration can be obtained. The sample container 10 must, therefore, always be filled with the same amount in order to be able to obtain reproducible results. Advantageously it should always be filled to the maximum. In some assay formats which may be carried out, the specific biocomponent is respectively on the surface of the sample container 10, and through contact with the liquid sample, it detaches itself from the surface and gets into the sample. Moreover the biocomponents can also be found on additional solid phases in the sample container 10. A simple and already known method consists in applying lyophilised antibodies to the surface of the sample container 10. In this way, it becomes possible to store the whole for a relatively long time before the immunoassays are actually carried out. The receiving region 2 defines the surface on the base plate on which, according to the assay format, the respectively corresponding chemical or biochemical substances are immobilised.

Figure 4:
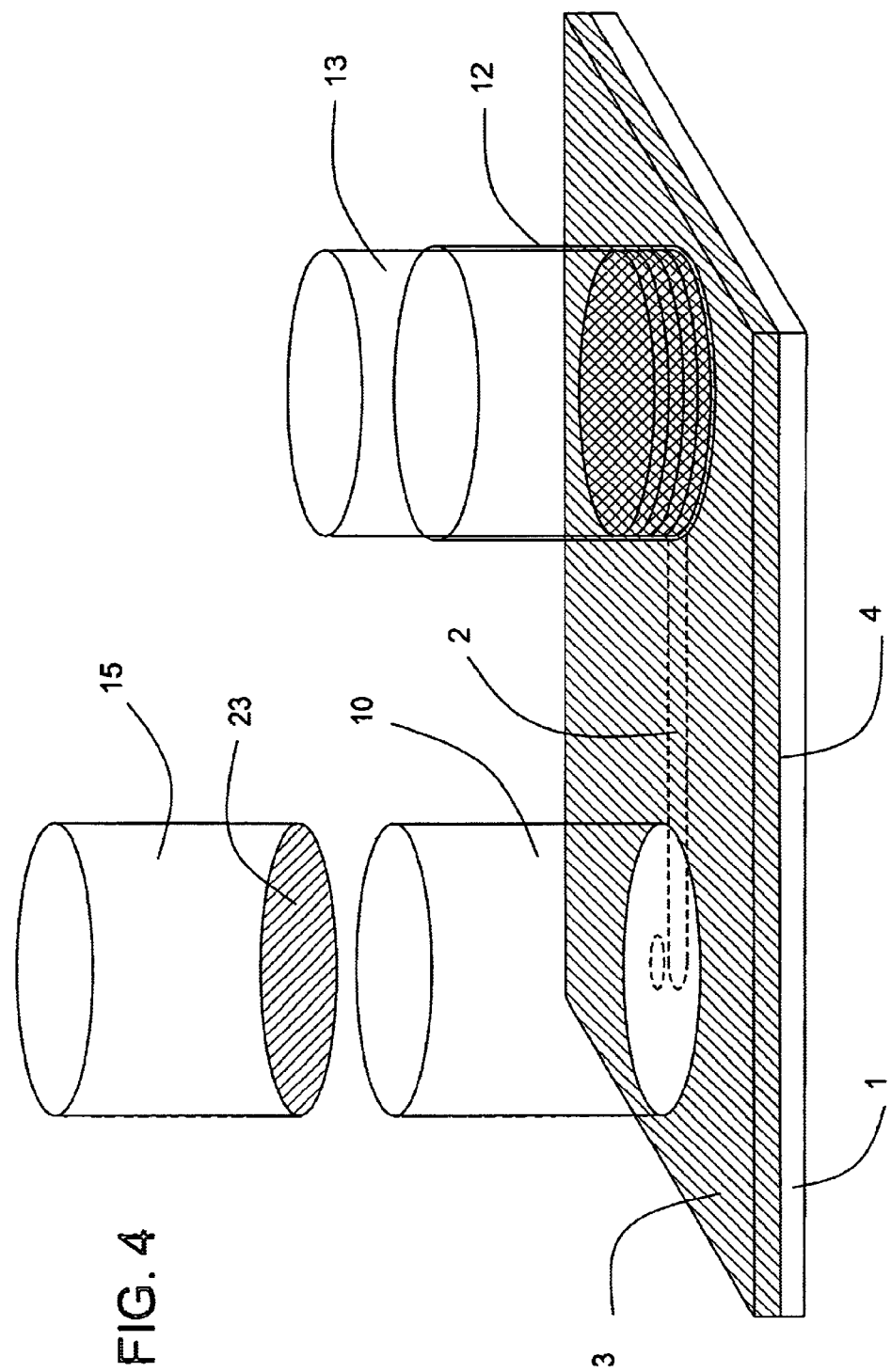
FIG. 4 a device with cylindrical hollow body.

In FIG. 4 is also represented a preferably cylindrical hollow body 12, in which a piston 13 or some other suitable covering is received, which both serve together as a pump. If the piston 13 moves out of the cylindrical hollow body 12, a negative pressure is produced which sucks the sample material out of the sample container 10 through the receiving region 2 in a direction towards the cylindrical hollow body 12. The flow is maintained by capillary forces in the receiving region 2 and by an absorbent fleece, until the entire sample volume is conveyed through the receiving region 2. The cylindrical hollow body 12 is set-on or has a hole in its base, such that a connection to the receiving region 2 is present. This can be realised through the second aperture 11 as a connection possibility in the covering plate 3. If no covering plate 3 is used, the connection possibility can also be configured in another manner.

However, an external pump can also be connected to aperture 11.

After application of the sample (with the sample container 10), a corresponding time must be waited such that the desired binding between the partners of a general receptor-ligand system can take place completely. Thereafter, the pump 12, 13 is activated and one waits until all the liquid has been pumped through the receiving region 2. After excitation with light source 7 or light sources 7 and 7', the antigen concentration can then be determined, and for this the structure according to the invention, as represented in FIG. 2, is to be used.

Some embodiments add a filter 23 to the configuration of FIG. 4. The filter 23 is fixed to the bottom of a hollow shaft 15. By removing particles, the filter 23 prevents the receiving region 2 from clogging.

The structure, as previously shown and described, can be used for the most varied biochemical assays, and further examples will be returned to.

Figure 5:
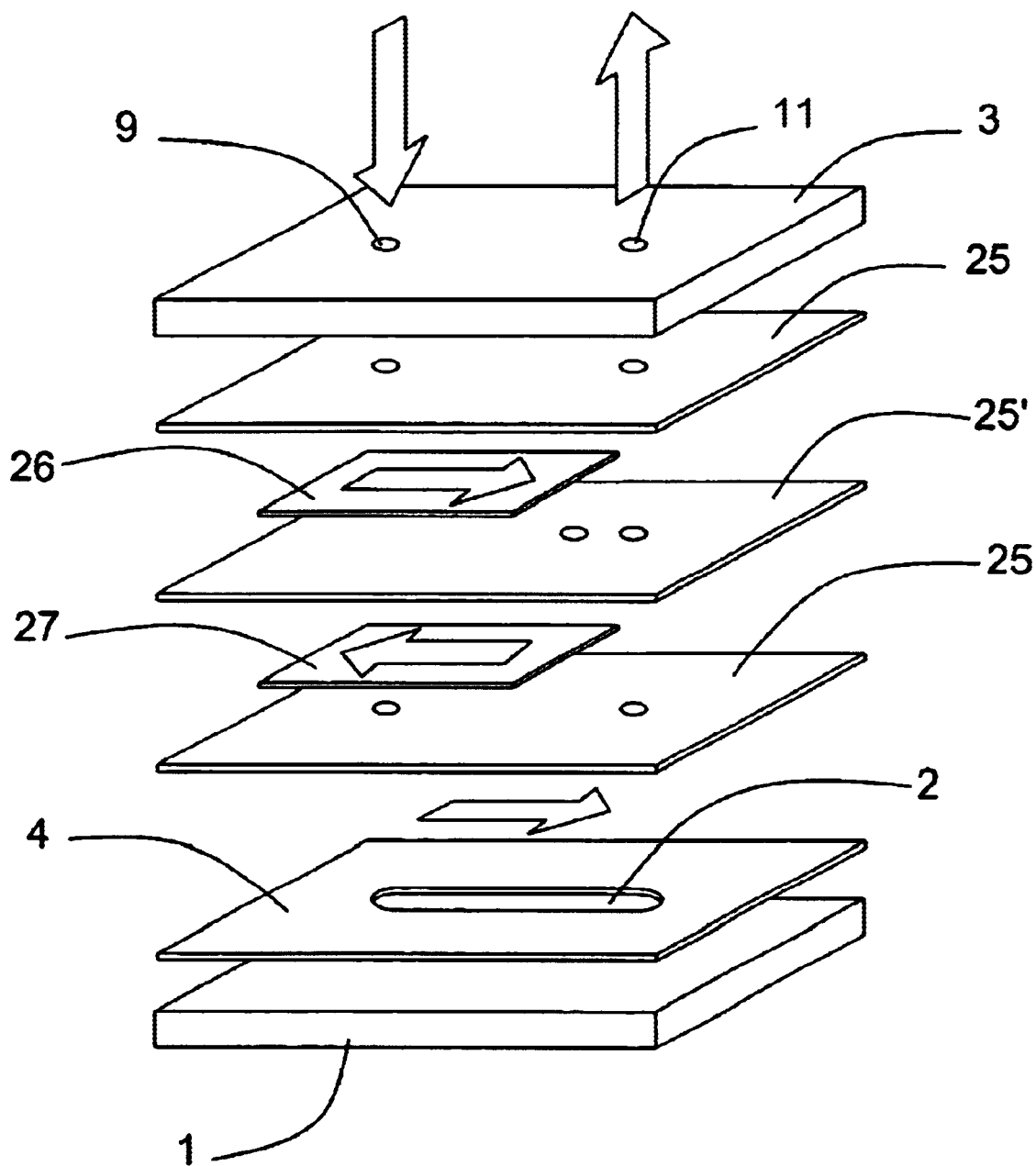
FIG. 5 a device with additional functional layers, with lateral flow.
Figure 6:
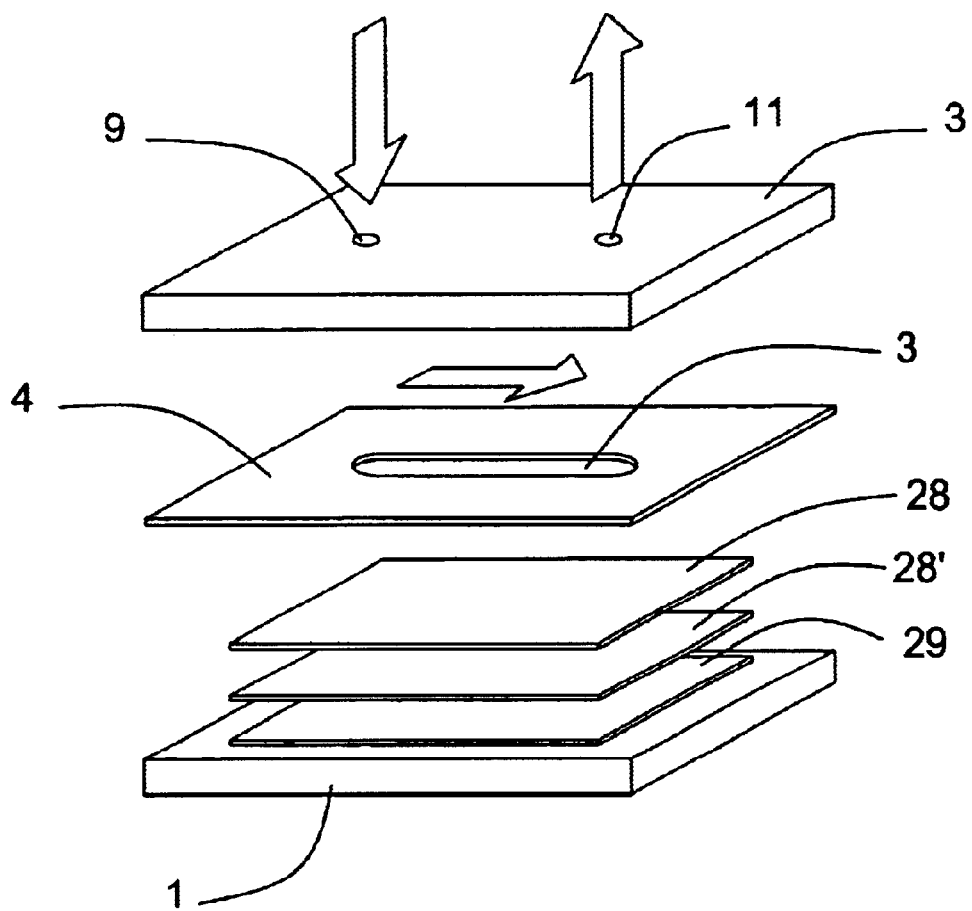
FIG. 6 a device with a plurality of functional layers and transverse flow.

As can be seen especially from FIGS. 1, 5 and 6, the essential part of the device according to the invention can be designed in very variable ways. Thus the different elements (plates, layers) can be composed of a kit in the most varied configurations and correspondingly be made available for different assay formats in situ, according to requirements.

Thus FIG. 5 shows an example of a device according to the invention, in which additional functional layers with lateral flow are represented. Here, in addition, functional layers 26 and 27 and separating layers 25, 25' are incorporated in the structure already explained in the description of FIG. 1. In this example, two functional layers 26 and 27 were disposed the one above the other, being enclosed on all sides by separating layers 25 and 25'. The separating layers 25 and 25' can here preferably be configured as adhesive films, in which openings are formed, as already described in the other place. These openings serve to make possible a connection between inlet aperture 9, the functional layers 26, 27, the receiving region 2 and the outflow aperture 11. The arrows drawn in FIG. 5 reproduce the direction of flow here.

Adaptation to different assay formats can be achieved by variation of the arrangement or selection of the functional layers 26, 27. Thus the functional layers 26 and 27 can be, for example, a reagent reservoir or a pure reaction layer.

However, there also exists the non-represented possibility of arranging at least two different functional layers in one plane, such that they can be flowed through in succession.

The structure shown in FIG. 6 of a portion of a device according to the invention differs from the example shown in FIG. 5 in that a transverse flow can be achieved. In this example, three functional layers 28, 28', and 29 are disposed the one directly above the other, i.e., without separating layers, directly on the base plate 1. Within the stack of layers so formed from functional layers 28, 28', and 29, the spacer 4 with the cuvette-shaped receiving region 2 is, in this example, disposed underneath the covering plate 3. Here, too, the arrows drawn in FIG. 6 indicate the direction of flow.

Differently from the structure shown in FIG. 6, other arrangements which ensure transverse flow can, of course, also be constructed. As already mentioned, the functional layers can be varied in their number, arrangement and choice of function. In an opposite manner to the shown example, the arrangement can also be designed above the spacer 4.

In this example, too, separating layers can be used, but it must be borne in mind that transverse flow must not be hindered. The functional layers can again serve as reagent reservoir or reaction layer.

The functional layers to be used according to the invention have here the advantage that a complete, integrated measuring system is produced and only the sample has to be led through the structure.

Combinations of transverse and lateral flow (combination of the examples in FIGS. 5 and 6) are also possible.

The functional layers 26, 27, 28, 28', and 29 can be used for the tasks of preparing the samples (buffering, filtration, separation, elimination of interferences, amongst other things), can be used as reagent carrier layer (e.g., for conjugate release) or as a reaction layer (e.g., for derivatization, for immobilisation of biocomponents or for the course of chemical or immunochemical reactions).

Suitable materials for the different functional layers are:

for the sample preparation—e.g., membranes made of fibrous material to separate plasma and red blood corpuscles, which are available, for example, from the company Pall Biosupport as "Hemadyne-Membran". However, filter papers made of cellulose or regenerated cellulose can also be used for this function.

reagent carrier layer—for this, paper made from 100% cellulose can also be used, or activated nylon 66, it being possible for the surfaces to be activated or modified in order to alter the flow properties (commercially available from the company Pall Biosupport under the trade name "Prodyne oder ACCUWIK-Membrane"), or, specially for lateral flow systems, polyester carriers with a modified surface and in which the flow properties may be controlled.

reaction layers—as so-called nitroflow membranes made of nitrocellulose, PVDF (polyvinyl difluoride) membrane (commercially available from the company Millipor with the trade name "Immobilon"), and here, too, the surface can be modified.

In general, fibrous materials, cellulose, nitrocellulose, polypropylene, polycarbonate, polyvinyl difluoride, hydrogels (e.g., dextran, acrylamide, agar—agar, carrageenan, alginic acid), polyelectrolytes (e.g., acrylic acid, poly-L-lysine, poly-L-glutamic acid) or nuclear track membranes or glass-fibre membranes can be used.

Figure 7:
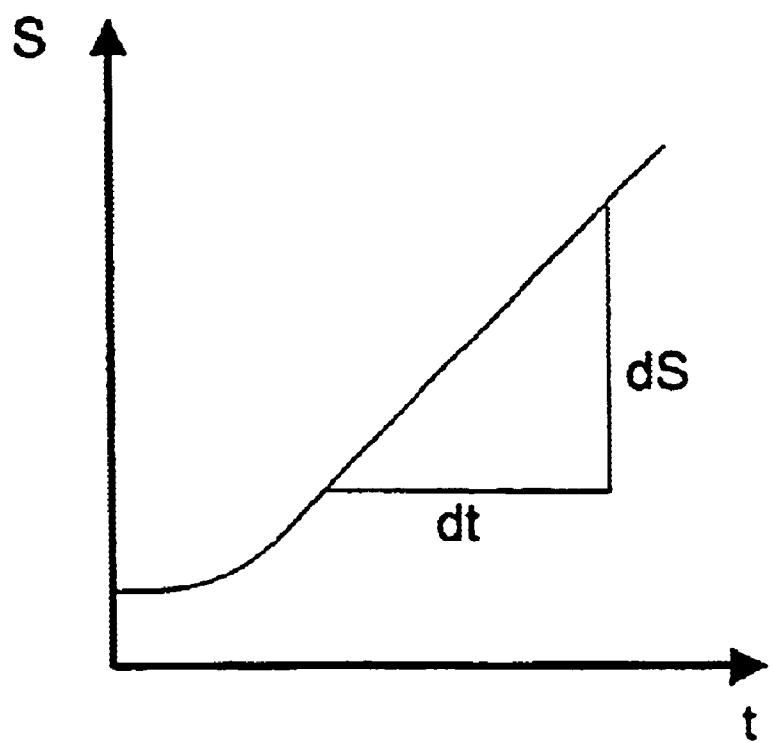
FIGS. 7 & 8 time-dependent fluorescence intensity patterns.
Figure 8:
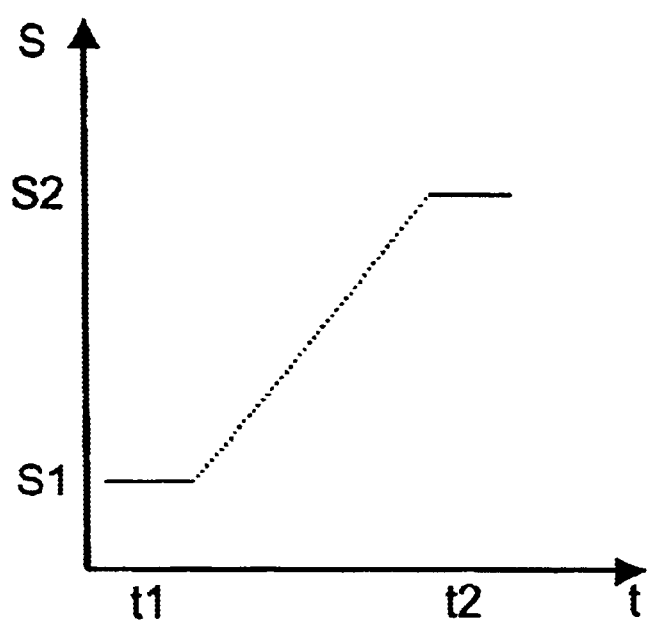

Basic possible ways of evaluating the measurement signals are represented in FIGS. 7 and 8.

In FIG. 7, the intensity of the measured fluorescence signal is shown dependent on time. With the linear rise in the intensity of the fluorescence signal, it suffices to determine the signal rise by differentiation, since the rise can be correlated with the temporal alteration in the amount of fluorophore, which can be measured with the device according to the invention. In this way, the measuring time can be kept very short, since the rise in the intensity of the fluorescence only has to be determined over a short period of time, independently of whether this takes place at the beginning or a later point in time, in carrying out the chemical or biochemical assay. Only the saturation range has to be borne in mind, and care taken that the measurement is only carried out in a time domain in which a temporal alteration of the fluorescence intensity signal can be detected.

Differing from this, another possibility is represented in principle in FIG. 8. Here the difference between an initial and a final value is formed and used for evaluation. A basic signal $S_1$ is first received before the addition of the analyte to be determined at time $t_1$ and, following the addition of the analyte, at a point of time $t_2$, which can be predetermined, a final value $S_2$ of the measured fluorescence intensity is determined. The analyte concentration can then be determined through the difference of the values $S_2$ and $S_1$. The difference between the times $t_2$ and $t_1$ must here be so great that an equilibrium has formed.

In FIGS. 9 to 16 are represented possible assay formats which can be carried out with the invention.

Figure 9:
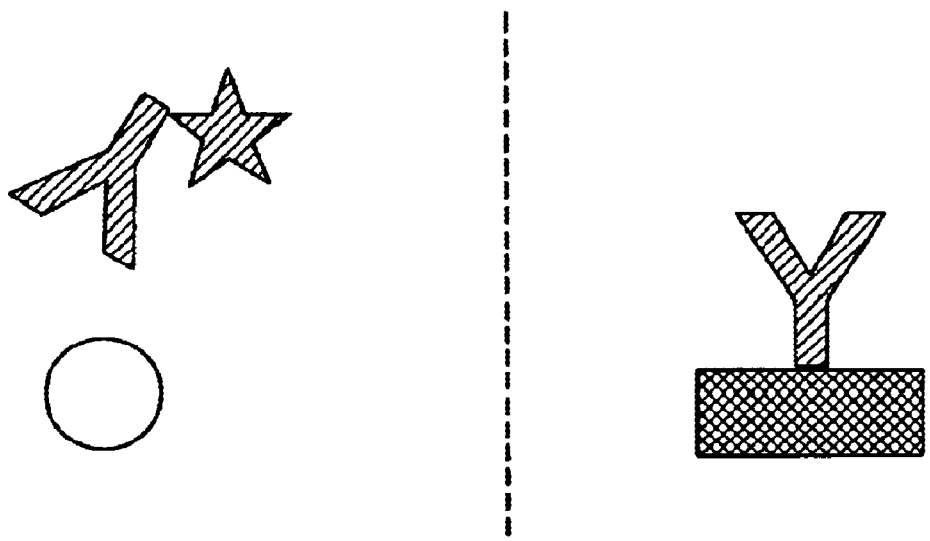
FIG. 9 a sandwich assay format.

FIG. 9 here shows a sandwich assay format which is practically only suitable for high-molecular compounds (proteins, amongst other things).

This sandwich format can here be carried out in principle in a device, such as represented in FIG. 5 or FIG. 6, in which at least one functional layer is to be used.

The analyte is here first to be incubated with the marked antibody and then led into the detection region of the base plate 1 for evanescent field excitation and corresponding fluorescence.

Another possible way of carrying out a sandwich assay format in sequential form is so executed that first the analyte and then the marked antibody form the sandwich step by step.

Further possible ways of immobilising the antibody in the base plate region are:

1. adsorption;
2. covalent bonding;
3. affinity bonding (e.g., A-protein A/G or after biotinylation to avidin); and
4. by hybridisation of a nucleic acid marker located on the antibody (single-strand RNA or DNA) to an immobilised single-strand nucleic acid (RNA or DNA) with complementary sequence.

Coating the base plate region, for the evanescent field excitation, with protein A/G, avidin, amongst other things, moreover, offers the possibility of producing a universal element (for the most varied analytes).

A particularly advantageous embodiment provides the pre-incubation of the analyte with a biotinylised (collector) antibody and a fluorescence-marked (detector) antibody. The two antibodies can, for example, be released simultaneously or in sequence from functionalised layers. The whole immunocomplex is then bound by binding to a sensor surface coated with avidin (alternatively streptavidin or neutravidin). Critical for signal formation is the very high affinity between biotin and avidin; this leads to an improvement in the sensitivity of the assay.

In this embodiment, a device according to FIG. 2 can also be used in conjunction with two different marking substances, and thus the determination of concentration for two different analytes can be carried out quasi simultaneously, also independently of the respective binding sites in the receiving region, such that the binding of the marked biocomponents does not have to take place locally selectively.

Figure 10:
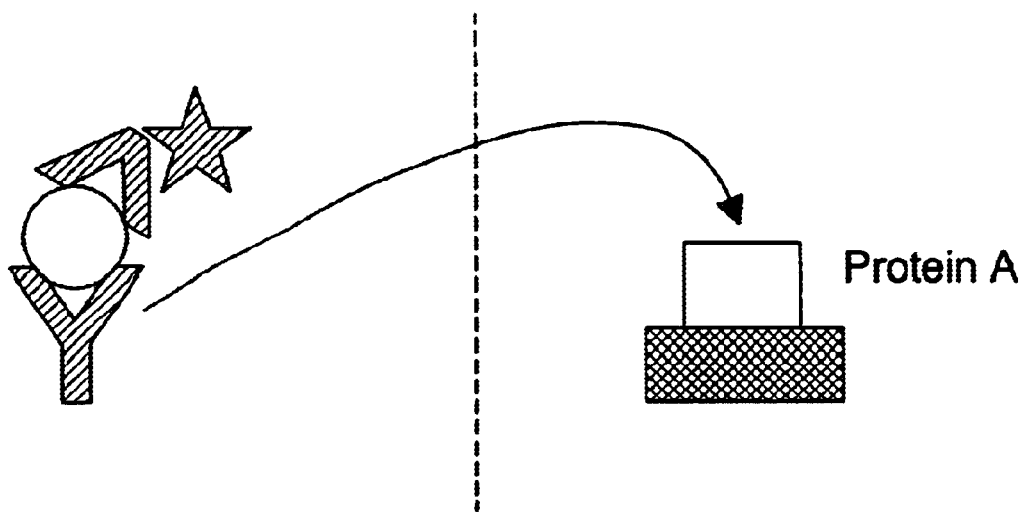
FIG. 10 a further sandwich assay format.

However, an assay format can also be carried out in which an antibody and a marked antibody fragment (e.g., an Fc-part or an ScFv-fragment) are incubated simultaneously with the analyte, as is shown in FIG. 10. There, only the complete antibody binds (to protein A/G or, after biotinylation, also to avidin), and thus the necessity for an incubation disappears. With this format there is the basic possibility of regenerating the structure used. This is not possible with avidin/biotin, however.

In the simultaneous incubation of analyte, antibody and marked antibody fragment in a sandwich assay, as is shown in FIG. 10, the marked antibody fragment and the antibody can be contained, for example, in functional layer 27, of the example shown in FIG. 5.

Instead of immobilising a collector antibody, other biocomponents, binding the analyte, can also be immobilised (e.g., protein A/G in the case of a sandwich assay for determining antibodies).

In all the sandwich assay formats, a directly proportional correlation between the signal and the concentration of the analyte occurs.

One or more components of the immunochemical reaction can, moreover, be prepared on functional layers, such as is the case for conjugate release, for example.

Figure 11:
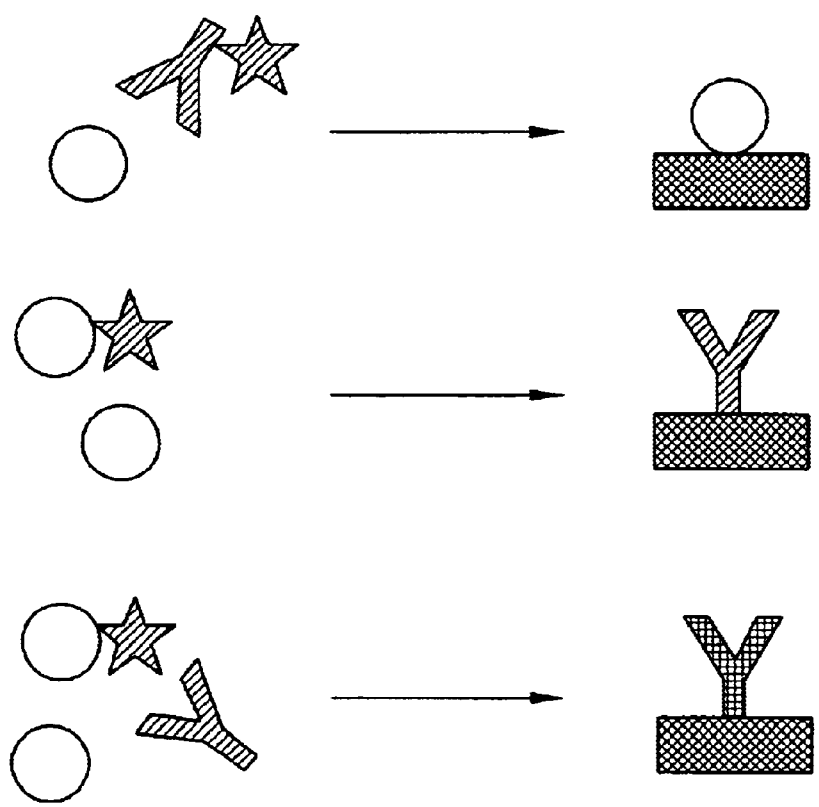
FIG. 11 a titration or competition assay format.

In FIG. 11 are represented possibilities for titration/competition formats, which differ from one another through sequential or simultaneous incubation of the immunocomponents. These two assay formats are suitable in particular for determining low-molecular compounds which cannot form a sandwich.

Moreover, the assay formats shown in FIG. 11 have no directly proportional correlation between the analyte concentration and the intensity of the measured fluorescence signal. There is thus an inversely proportional correlation.

Thus, in the upper example shown in FIG. 11, the marked antibody can be present, for example, in the functional layer 27 in the example shown in FIG. 5.

The middle example of FIG. 11 can be so configured that a marked analyte can be contained, e.g., also in this layer. The lower representation of FIG. 11 can be so implemented that a marked analyte is contained, for example, in functional layer 26 and an antibody in layer 27 of the example shown in FIG. 5. However, the implementation of the lower example shown in FIG. 11, can also be carried out in such a way that an antibody is contained in functional layer 26 and the marked analyte in layer 27 in the example shown in FIG. 5.

From this it follows that, in the assay formats shown in FIG. 11, either the analyte or the antibody can be immobilised (cf. upper and middle examples of FIG. 11). Therefore the methods described for the sandwich assay formats can also be used, at least partially. Thus a generic anti-antibody (cf. lower example in FIG. 11) or protein A/G (after biotinylation of the specific antibody, also avidin) can be immobilised. In this case, the immobilised biocomponent serves exclusively to enrich the added specific antibody and can therefore be immobilised in excess.

Further assay formats having directly proportional correlation between analyte concentration and fluorescence signal intensity will be described below.

For this, there are basically two possibilities, it being possible to carry out the respective assay with an additional solid phase or in solution.

Figure 12:
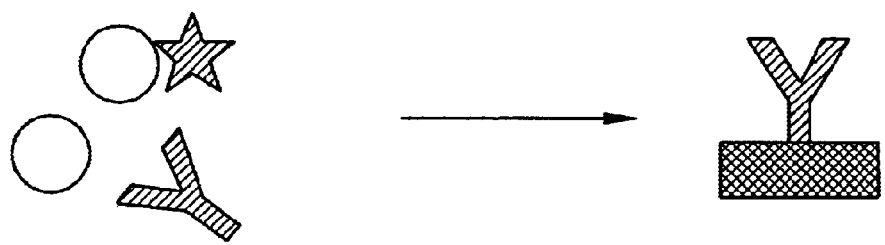
FIGS. 12 & 13 a competition or displacement assay format with directly proportional ratio of analyte concentration and signal intensity.

For example, all the components can be incubated in solution. The assay format shown in FIG. 12 provides for a pre-incubation of the reactants and the forming of a binding equilibrium. A free analyte competes with the marked analyte for binding to the antibody, the same antibody being immobilised on the base plate 1 in the detection region as is also contained in the solution.

The immobilisation can be carried out as in sandwich assay formats.

Since only free, i.e., not antibody-bound, marked analyte is determined, a directly proportional correlation between the analyte concentration and the fluorescence signal results.

Moreover, the immobilised biocomponent serves exclusively to enrich the hapten-fluorophore conjugate and can thus be immobilised in excess. Through immobilisation of a specific antibody, a corresponding structure of the device according to the invention can, however, only be used for respectively one analyte.

The assay format shown in FIG. 12 can be carried out with a device such as is shown in FIG. 5, if a marked analyte is contained in functional layer 26 and antibody in functional layer 27.

Figure 13:

For the case where, instead of the marked analyte, a marked analyte analogue is used, which has a clearly reduced affinity to the antibody, a displacement assay, already described, can be carried out. This is shown in FIG. 13. A marked analyte or an analyte analogue can here be contained, for example, in functional layer 28 of the example shown in FIG. 6.

However, an additional solid phase can also be exploited, which can be accommodated either in a separate reaction space or as a functional layer directly on the detection region of the base plate 1.

The additional solid phase can in principle exercise the same functions as the functional layers.

The use of a separate reaction space (e.g., an incubation test tube) such as the sample container 10, which is shown in FIGS. 3 and 4, has the advantage that generic structures, i.e., structures utilisable for all the analytes, can be used.

On this universal structure, not a specific but a generic anti-antibody or protein A/G, avidin (after biotinylation of the antibody), amongst other things, is immobilised. Since only one biocomponent above the base plate 1 is enriched, the immobilised components can be applied in excess.

The procedure can, in general, be such that one of the immunocomponents (the marked antibody or marked analyte) is kept back on a solid phase, for example a functional layer with hapten-protein conjugate. Only in the presence of free analytes is a portion of the marked components not bound to the solid phase and can then be measured above the base plate 1 in the detection region. These circumstances are represented schematically in the example shown in FIG. 14.

Figure 14:
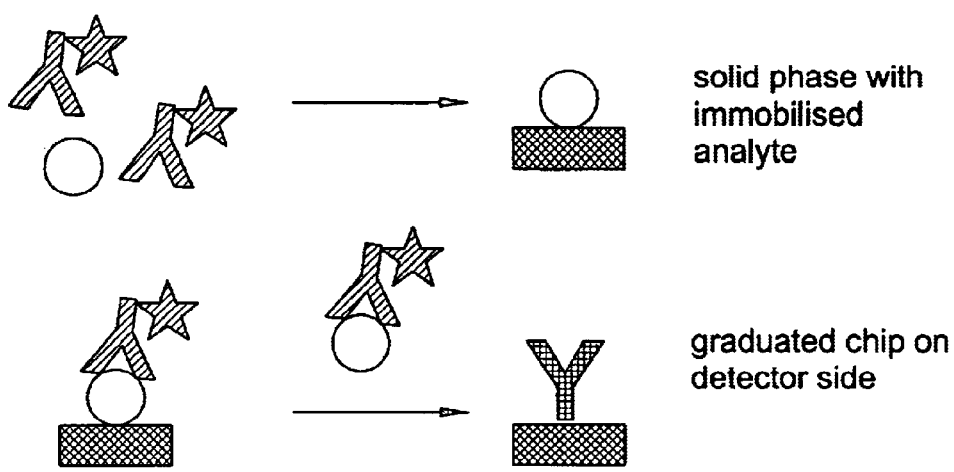
FIG. 14 an assay format using an additional solid phase.

Here free analyte and analyte immobilised on the solid phase compete for binding to the specific antibody, as is shown in a first step in FIG. 14, at the top.

The solid phase is only passed by antibodies which have bound beforehand to analyte, as is represented in the lower part of FIG. 14. Consequently, only analyte-bound antibody can be detected, for example by a generic anti-antibody. Here, too, there is a directly proportional correlation between the analyte concentration and the intensity of the measured fluorescence.

If, in the concrete case of FIG. 14, a membrane is used as the additional solid phase, which is integrated into the structure, functional layer 26 (reservoir for the marked antibody) and the solid phase as layer 27 of the example shown in FIG. 5 can be used in the example shown in FIG. 14.

Various materials can serve as solid phases, and of these, in particular membranes can be easily integrated as functional layers. Such membranes can be nitrocellulose, immunodyne, conjugate release membranes, regenerated cellulose, amongst other things. Here the respective biocomponent can be immobilised by adsorption, covalent bonding or by affinity bonding. Haptens can be immobilised as hapten-protein conjugate.

As opposed to membranes with transverse flow, membranes with lateral flow and packed columns offer advantages through repeated establishment of equilibrium and render possible a quantitative binding of the biocomponents. Suitable materials for packed columns are sepharose, porous media, amongst other things.

The wall of a possibly utilisable vessel, for example the wall of the sample container 10 mentioned, or the supply pipes can also serve as the solid phase and be, for example, polystyrene vessels or glass capillaries. So too, can particle suspensions, in which the sample can be a suspension with solid particles (magnetic particles, latex, amongst other things). These particles can be separated through the application of a magnetic field or through subsequent filtration.

With the invention it is also possible to carry out so-called displacement assay formats, two variants of this being in principle possible. The displacement can here take place on an additional solid phase in a functional layer or externally, i.e., not in an integrated functional layer, or directly on the base plate 1 in the detection region.

Figure 15:
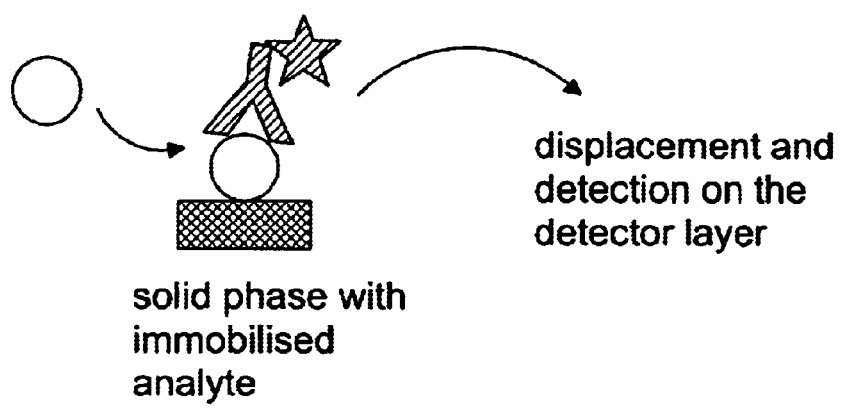
FIG. 15 a displacement assay with additional solid phase.

In FIG. 15, an example of a displacement assay with additional solid phase is represented in principle. The solid phase can be either the sample container 10 mentioned, a supply pipe or a functional layer. A marked antibody or analyte is here bound through specific ligand/receptor action. Through the addition of a free analyte, the displacement of the biocomponent can be achieved.

The solid phase can be, for example, functional layer 26 in the example according to FIG. 5.

In the example shown in FIG. 15, the marked antibody is bound on the base plate 1 in the detection region by a generic anti-antibody or protein A/G, avidin, amongst other things.

If, however, the opposite procedure is carried out and a marked analyte is bound to an immobilised antibody and then displaced, in the detection region on the base plate 1, a specific antibody, directed against the analyte, is immobilised. Since in every case the displaced component is always detected, there is a direct proportional correlation between the concentration of the respective analyte and the fluorescence signal intensity.

The displacement can, however, also be carried out directly in the detection region on the base plate 1 as a very simple assay configuration, since only one sample is guided through the element.

Figure 16:
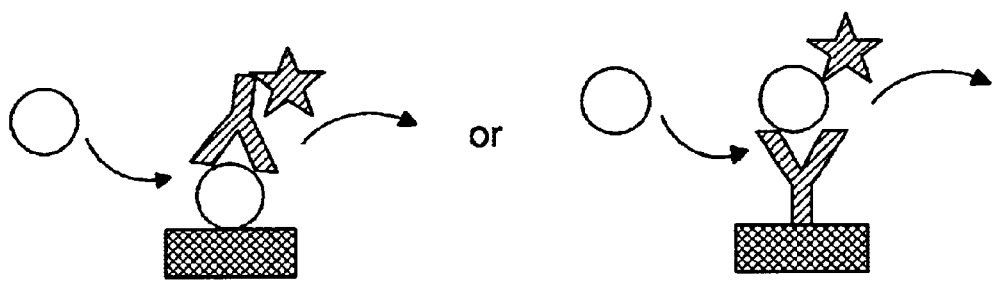
FIG. 16 a further displacement assay.

No pre-incubations or similar steps take place. Conditioning of the sample can be achieved through integration of corresponding functional layers. Here, also, two different possible ways of immobilising the analyte or the specific antibody present themselves, as is shown in FIG. 16.

Here, respectively the decrease in the fluorescence intensity signal is measured, such that an inversely proportional correlation between the analyte concentration and the fluorescence signal intensity occurs. The absolute value of the rise in the fluorescence intensity signal is, however, directly proportional to the analyte concentration and can be evaluated in the form already described.

Figure 17:
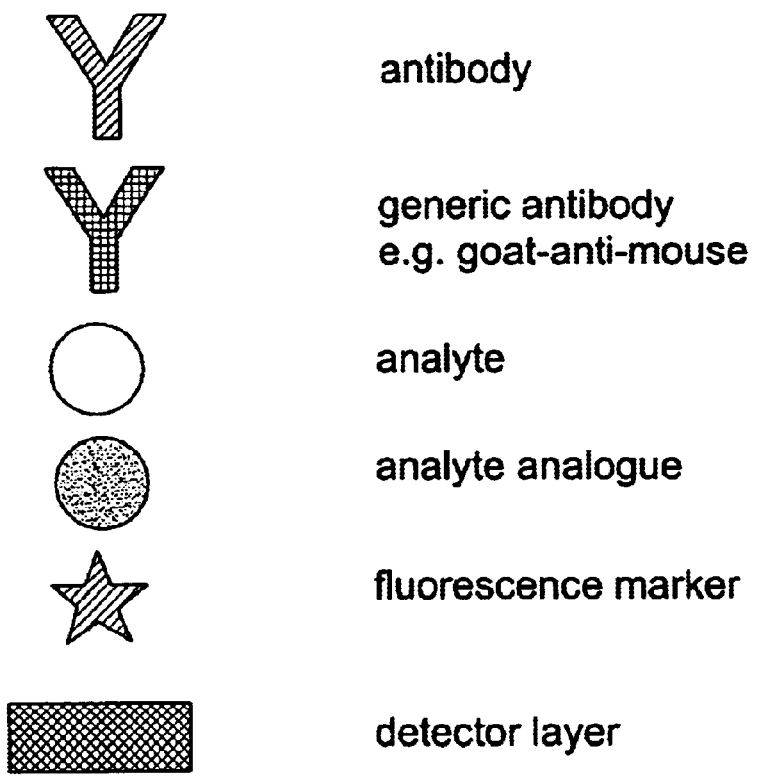
FIG. 17 a general key to the assay formats shown in FIGS. 9 to 16.

FIG. 17 serves as a general key for the different assay formats shown in FIGS. 9 to 16.

We claim:

1. A device for carrying out fluorescence immunoassays by means of evanescent field excitation, the device comprising:
    an optically transparent base plate;
    a receiving region for a sample;
    a boundary surface between the base plate and the receiving region, the base plate having a refractive index greater than that of a material above the boundary surface;
    a plate covering the receiving region on a side opposite the base plate;
    a functional layer between the base plate and covering plate or in an inflow region for the sample into the receiving region, flowed through laterally or transversally by means of suction, pressure, or capillary force;
    a light source, emitting practically monochromatic light, directing light rays with a wavelength causing fluorescence of a marking substance bound to a chemical or biochemical partner of a receptor-ligand system onto the boundary surface on a side of the base plate opposite the covering plate; and
    a fluorescence detector disposed on the side of the base plate opposite the covering plate, the fluorescence detector disposed to detect fluorescence passing through the base plate and then passing through air to the fluorescence detector, the fluorescence detector not disposed to detect fluorescence coupled into the base plate acting as a waveguide.

2. The device according to claim 1, further comprising:
    a spacer between the base plate and covering plate forming the receiving region.

3. The device according to claim 1, further comprising:
    an inlet aperture and an outlet aperture in the covering plate.

4. The device according to claim 3, wherein a plurality of functional layers, separated by separating layers, are disposed alternating one above another, making possible a connection of the inlet and outlet apertures via the receiving region by means of openings.

5. The device according to claim 4, wherein at least two different functional layers are disposed beside one another in one plane.

6. The device according to claim 1, wherein the functional layer consists of fibrous material, cellulose, nitrocellulose, polypropylene, poly-carbonate, polyvinyl difluoride, or of a hydrogel, or of polyelectrolytes, or of track-etch membrane or glass fibre membranes, or is configured as a packed column.

7. The device according to claim 1, wherein at least one functional layer in the receiving region is in direct contact with the base plate.

8. The device according to claim 1, wherein a plurality of functional layers are disposed one directly above another.

9. The device according to claim 1, further comprising:
a sample container that defines a sample volume, the sample container so disposed that a formed between the receiving region and sample container.

10. The device according to claim 9, wherein a solid phase is formed in the sample container, in an inflow region, in the receiving region, or as a functional layer.

11. A method of carrying out fluorescence immunoassays by means of evanescent field excitation, the method comprising:
guiding a sample volume by means of suction, pressure, or by capillary forces, through at least one functional layer and thereafter through a receiving region;
emitting light with a wavelength causing fluorescence of marked chemical or biochemical components bound to a surface in the receiving region; and
measuring fluorescence with a detector, the detector disposed to detect fluorescence passing through a base plate adjoining the receiving region and then passing through air to the detector, the detector not disposed to detect fluorescence coupled into the base plate acting as a waveguide.

12. The method according to claim 11, wherein the at least one functional layer carries out a function from the group consisting of filtration, separation, elimination of interfering substances, and release of reagents.

13. The method according to claim 11, wherein a rise in a measured fluorescent light intensity correlates with and is used to determine an analyte concentration.

14. The method according to claim 11, wherein a difference between two fluorescence intensity signals, measured in intervals, is used to determine an analyte concentration.

15. The method according to claim 11, wherein with the sample volume is carried out a biochemical assay of a receptor-ligand system selected from the group consisting of: antigen-antibody, lectin-carbohydrate, DNA-complementary nucleic acid, RNA-complementary nucleic acid, DNA-protein, RNA-protein, hormone-receptor, enzyme—enzyme cofactors, protein G-immunoglobin, protein A-immunoglobin, and avidin-biotin.

16. The method according to claim 11, wherein a sandwich assay is carried out by:
leading an analyte into the receiving region, at least some of the analyte binding to the bound chemical or biochemical components; and
leading a marked antibody into the receiving region, at least some of the marked antibody binding to the analyte, wherein there is a direct correlation between an amount of measured fluorescent light and a concentration of the analyte in the receiving region.

17. The method according to claim 11, in which a competition assay is carried out by:
leading an analyte into the receiving region, at least some of the analyte binding to the bound chemical or biochemical components; and
leading a marked test compound into the receiving region, at least some of the marked test compound binding to the bound chemical or biochemical components, wherein there is an inverse correlation between an amount of measured fluorescent light and a concentration of the analyte in the receiving region.

* * * * *

UNITED STATES PATENT AND TRADEMARK OFFICE
CERTIFICATE OF CORRECTION

PATENT NO. : 6,686,208 B2
DATED : February 3, 2004
INVENTOR(S) : Meusel et al.

It is certified that error appears in the above-identified patent and that said Letters Patent is hereby corrected as shown below:

Title page,
Item [56], References Cited, FOREIGN PATENT DOCUMENTS,
-- DE 196 28 002 — 12/18/97 -- should be inserted.

Column 13,
Line 12, "sample container so disposed that a formed between" should read -- sample container so disposed that a connection is formed between --.

Signed and Sealed this

Twenty-seventh Day of July, 2004

JON W. DUDAS
*Acting Director of the United States Patent and Trademark Office*